United States Patent [19]
Sleath et al.

[11] Patent Number: 5,670,167
[45] Date of Patent: Sep. 23, 1997

[54] PROCESS FOR THE PRODUCTION OF MEDICAMENT FORMULATIONS

[75] Inventors: Clive Roland Sleath, Mountsorrel; Paul Manuel Anson, Chesterton; Hugh William Dyson, Haddenham, all of United Kingdom

[73] Assignee: Fisons plc, Ipswich, United Kingdom

[21] Appl. No.: 624,590

[22] PCT Filed: Oct. 10, 1994

[86] PCT No.: PCT/GB94/02214

§ 371 Date: Jun. 17, 1996

§ 102(e) Date: Jun. 17, 1996

[87] PCT Pub. No.: WO95/10407

PCT Pub. Date: Apr. 20, 1995

[30] Foreign Application Priority Data

Oct. 8, 1993 [GB] United Kingdom ............... 9320795
Jul. 21, 1994 [GB] United Kingdom ............... 9414692

[51] Int. Cl.⁶ .................................................. A61K 9/20
[52] U.S. Cl. .................. 424/464; 424/1.13; 424/434
[58] Field of Search ............................. 424/464, 489, 424/1.13, 434

[56] References Cited

U.S. PATENT DOCUMENTS 3,189,942  6/1965  Rapprich ........................... 425/78

FOREIGN PATENT DOCUMENTS

| 0407028 | 5/1990 | European Pat. Off. . |
|---|---|---|
| 0 407 028 | 1/1991 | European Pat. Off. . |
| 0 450 784 | 10/1991 | European Pat. Off. . |
| 1963367 | 6/1965 | Germany . |
| 55138002 | 10/1980 | Japan . |
| 56000204 | 1/1981 | Japan . |
| 587577 | 4/1947 | United Kingdom . |
| WO 94/00291 | 1/1994 | WIPO . |

Primary Examiner—Thurman K. Page
Assistant Examiner—William E. Benston, Jr.
Attorney, Agent, or Firm—Ross J. Oehler

[57] ABSTRACT

A medicament compact is produced by placing loose powdered medicament in a mould having a longitudinal axis where a mandrel is positioned along the longitudinal axis of the mould compressing the medicament when a force parallel to the longitudinal axis is applied. The frictional force between the medicament and the mould and the frictional force between the medicament and the mandrel are opposite. Apparatus and compacted medicaments are also disclosed,

8 Claims, 3 Drawing Sheets

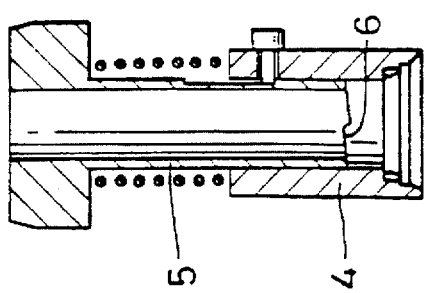
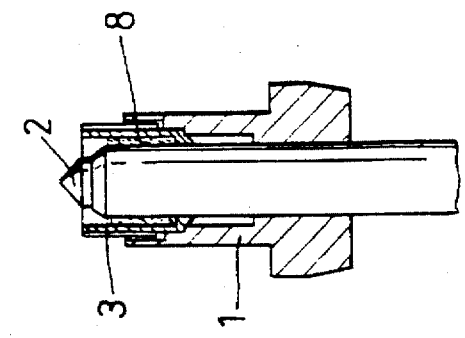
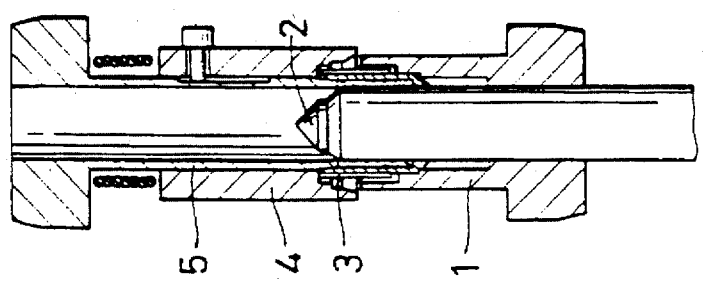
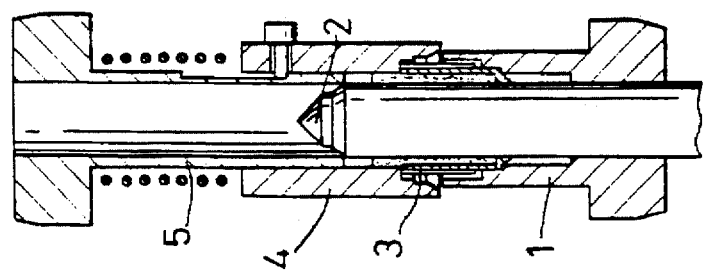
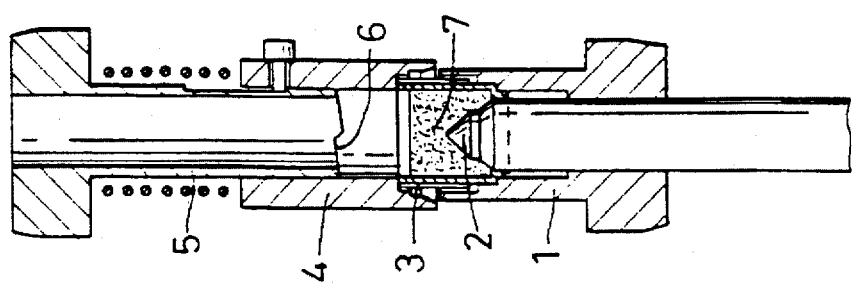
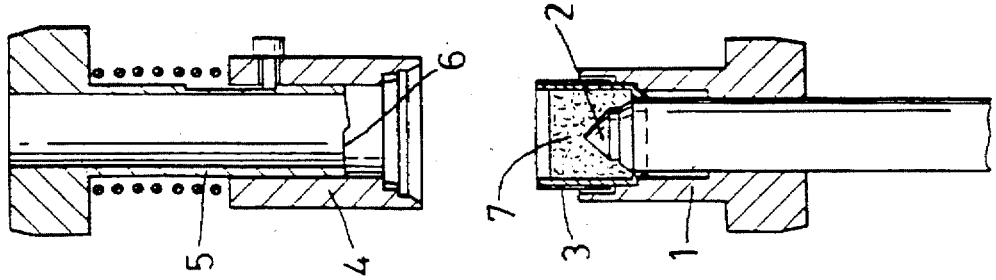
Fig. 2A  Fig. 2B  Fig. 2C  Fig. 2D  Fig. 2E

PROCESS FOR THE PRODUCTION OF MEDICAMENT FORMULATIONS

This application is a 371 of PCT/GB94/02214 dated Oct. 10, 1994.

This invention relates to a novel process for the production of a compacted body of powdered medicament, especially powdered inhalation medicament, referred to herein as a "medicament compact", of the type disclosed in European Patent 407028.

The administration by inhalation of medicaments in dry powder form is well known. Devices for the metering and dispensing of measured doses of medicament from a reservoir have also been described previously, for example, in UK Patent No. 2041763 and U.S. Pat. No. 2,587,215. Such devices typically comprise a medicament reservoir and a metering chamber with a volume chosen such that, when filled, the chamber contains the desired weight of medicament for one dose. Filling of the metering chamber is generally accomplished under the influence of gravity, the chamber typically being located at the bottom of the reservoir. Such devices have the disadvantage that variations in the density of the metered powder can easily occur resulting in inaccurate or inconsistent dosing. The packing density of the powder may also depend on the weight of powder remaining in the reservoir, leading to a gradual reduction in the dose delivered by the device. In addition, the dose metered is strongly dependent on the orientation of the device.

European Patent 407028 discloses a device which overcomes the disadvantages of other dry powder devices by the use of a metering means which relies not on gravitational force to fill a metering chamber, but on abrasion of a compacted body of powdered medicament. This application contemplated the use of hydraulic presses and the like in the production of the medicament compacts.

Since the device of European Patent 407028 (in which the medicament compacts are adapted for use) functions by abrading a fixed volume of the medicament compact, it is important that the density of medicament throughout the compact is as uniform as possible. If the density is uniform then slices of medicament of the same thickness abraded from the compact will contain the same amount of medicament, thus ensuring that the correct dosage of medicament is consistently administered to a patient.

Compacted bodies of powdered inhalation medicament are also disclosed in International Patent Applications WO 93/24165 and WO 94/14490. The later application (published after the priority date of the present application) contemplates methods involving isostatic compression of elastic matrices, injection moulding of plastified masses, melting processes and pressure diecasting for the production of such compacted bodies.

International Patent Application WO 94/00291, published after the priority date of the present application, describes a process for making annular compacted bodies of powdered medicament which involves the radial compaction of loose powdered medicament using an expanding mandrel.

We have now found a novel process for the production of medicament compacts which allows for the production of medicament compacts having a more uniform density than compacts produced by prior art processes and which overcomes or substantially mitigates the problems encountered in processes known from the prior art.

According to the invention we provide a process for the production of a medicament compact, which comprises the steps of:

a) placing loose powdered medicament in a mould having a longitudinal axis,
b) positioning a mandrel along the longitudinal axis of the mould; and
c) compressing the medicament by applying a force parallel to the longitudinal axis such that during compression the frictional force between the medicament and the mould and the frictional force between the medicament and the mandrel are in opposite directions parallel to the longitudinal axis.

Steps a) and b) may be performed in either order or simultaneously, however, we prefer the mandrel to be positioned along the longitudinal axis of the mould after the medicament has been placed in the mould. Positioning the mandrel along the longitudinal axis of the mould after the powder has been added ensures an even distribution of powder around the mandrel, placing the powder in the mould after the mandrel has been inserted is less likely to give an even distribution of powder.

It is preferable that the frictional force between the medicament and the mould and the frictional force between the medicament and the mandrel are in opposite directions parallel to the longitudinal axis for the entirety of the compaction step c).

The frictional force between the medicament and the mould and the frictional force between the medicament and the mandrel may be caused to be in opposite directions parallel to the longitudinal axis, by performing the process such that the mould and the mandrel move relative to one another in a direction parallel to the longitudinal axis during the compression process. The mandrel is preferably slidably mounted along the longitudinal axis of the mould. Relative movement can thus be achieved by fixing the position of the mandrel and moving the mould in a direction parallel to the longitudinal axis, or by fixing the position of the mould and moving the mandrel.

Compaction of the powder contained in the mould is preferably effected using compaction means, e.g. a compaction sleeve, adapted to fit around the mandrel and slide inside the mould, thereby providing a limiting wall for the area in which the powder is compacted. If the mandrel and the compaction means are held stationary relative to one another during the compaction of the powder, then the distance moved by the mould relative to the mandrel during the compaction process will be equal to or greater than the difference in height between the loose and compacted powder contained in the mould. In order to increase the distance moved by the mould relative to the mandrel during the compaction process, the compaction means may also be moved relative to the mandrel, in the same direction as, but to a lesser degree than, the mould.

Alternatively, increased relative movement of the mandrel and mould may be achieved by moving the mandrel and the mould in opposite directions during the compaction process.

To ensure that the frictional force between the medicament and the mould and the frictional force between the medicament and the mandrel are in opposite directions parallel to the longitudinal axis for the entirety of the compaction step there should be no pre-compaction of the powder prior to the relative movement of the mould and the mandrel, i.e. the compaction means should exert no force on the powder before the mould and mandrel begin to move relative to one another.

By ensuring that the frictional force between the medicament and the mould and the frictional force between the medicament and the mandrel are in opposite directions parallel to the longitudinal axis during compaction the process according to the invention has the surprising advantage that it produces medicament compacts having a more uniform density than compacts produced by prior art processes. Medicament compacts having a uniform density distribution are advantageous in that sequential volumes of medicament abraded from the compact, e.g. by the device disclosed in European Patent 407028, will have similar masses, thus resulting in improved uniformity of dose administered to the patient.

The process is also advantageous in that it allows medicament compacts to be produced in a single rather than a multi-step compaction procedure, it also allows the production of longer compacts having a more uniform density distribution.

The powdered medicament is preferably metered into the mould, e.g. by weighing the desired amount of medicament. Alternatively, medicament compacts of the desired total mass may be produced by cutting to the appropriate length.

When the mandrel is positioned along the longitudinal axis of the mould after the loose powdered medicament is placed in the mould, the mandrel preferably has a tapered end. Thus, during the powder filing step the mandrel is fully, or preferably partially, retracted from the mould and once the powder is in the mould it is pushed, tapered end first, through the powder displacing it from its original shape into a shape, e.g. an annulus, suitable for compaction.

Prior to compaction, it is preferable to level the surface of the powder contained within the chamber defined by the mould and the mandrel. This may be done by vibrating the compaction assembly and/or using a levelling device. This ensures that the powder has settled to a level height, i.e. that the surface of the powder is even, it can also assist in removing trapped air from the powder and in breaking up aggregates of powder. Vibration of the assembly may be achieved using an electro-magnetic or other vibrator. Vibration preferably occurs during step b) and starts before the mandrel is pushed fully through the powder. Vibration is preferably applied to the mandrel. The frequency of vibration may be in the range of 100 to 1000 Hz.

During vibration of the mould assembly it is desirable that any loose parts of the assembly should be held in position. This may be accomplished using mechanical clamping means, spring force, or by using a vacuum to hold such parts in place.

The pressure exerted by the compaction means will depend upon the desired density of medicament in the compact (by density of medicament we mean the mass of medicament per unit volume). However, the compaction means typically exerts a pressure of from $60\times10^3$ to $2000\times10^3$ N.m$^{-2}$, for example $900\times10^3$ N.m$^{-2}$. The apparatus for performing the process according to the invention may be provided with a load sensor, e.g. a load cell, to measure the compaction force. The load sensor may be positioned under the mould or on the compaction means.

The density of the medicament in the compacts produced according to the invention will depend inter alia upon the medicament used. However, a typical compact may have a density of from 0.1 to 1.5 g/cm$^3$. The density of the medicament compacts produced according to the invention may be determined by weighing a fixed volume of medicament abraded from the compact.

We prefer the medicament compact to be formed in a mould which subsequently forms all or part of the medicament reservoir of a medicament inhalation device. Thus, after compaction the compact and mould are in a form suitable for direct transfer to the inhalation device. By obviating the need to remove the compact from the mould prior to its insertion in the device, handling of the medicament compact, and hence the risk of contamination or loss of medicament through premature abrasion, is reduced.

After production the compact may be transferred directly to the inhalation device from which it is to be administered, alternatively the compacts may be packaged separately thus providing replacement medicament reservoirs for the device from which they are to be administered.

According to a further aspect of the invention we provide the novel apparatus described herein for carrying out the first aspect of the invention.

Therefore, we provide an apparatus for the production of a medicament compact from loose powdered medicament which comprises:

a) a mould having a longitudinal axis adapted to receive loose powdered medicament, b) a mandrel adapted to be positioned along the longitudinal axis of the mould; and c) means for compressing the medicament by applying a force parallel to the longitudinal axis such that during compression the frictional force between the medicament and the mould and the frictional force between the medicament and the mandrel are in opposite directions parallel to the longitudinal axis.

The apparatus according to the invention may be made from any suitable materials known to those skilled in the art. Suitable materials for the mandrel include stainless steel e.g. 316 grade, teflon coated stainless steel, silicon nitride, polyphenyl sulphide (PBS), acetal co-polymer, and especially polybutylene terephthalate (PBT) e.g. PBT containing 20% polytetrafluoroethylene (PTFE). Suitable materials for the compaction means, e.g. the compaction sleeve, include stainless steel and acetal co-polymer.

The relative movement of the various parts of the apparatus may be achieved mechanically, employing e.g. electrical or hydraulic power. Suitable drive means include e.g. a stepper motor or servo motor. Separate drive means are preferably provided for the mould and the compaction means. The drive means are preferably provided along the longitudinal axis of the mould and should ideally be controllable to speed, position, acceleration and deceleration. Typical drive speeds for the compaction assembly are, for positioning the mandrel along the longitudinal axis of the mould, 50 to 1000 mm/min; and, for compacting the medicament, 5 to 5000 mm/min.

When the medicament compact is for use in a device as disclosed in European Patent 407028 in which the metering means includes a helical blade for abrading the medicament compact, the face of the compaction sleeve which contacts the medicament compact is preferably provided with a helical profile having a pitch equal to that of device blade. Providing this helical profile means that in use the compact does not have to be "primed" by abrading several doses from it until the blade "beds-in", thus reducing wastage of medicament.

Medicament compacts produced according to the invention will generally be annular, i.e. cylindrical with a cylindrical inner space. The radial thickness of the medicament in such a medicament compact is preferably in the range of 0.2 to 20 mm, more preferably 0.5 to 5 mm, for example 2 mm. The cylindrical inner space preferably has a diameter of more than 10 mm and preferably less than 100 mm, for example 20 mm.

The length of the medicament compact will inter alia on its intended use and the number of doses of active ingredient it contains. For administration from a device as disclosed in European Patent Application No. 407028, a suitable length will be in the range 5 to 50 mm, e.g. 20 mm.

Active ingredients which may be incorporated in compacts produced according to the invention include any active ingredients which are conventionally administered by inhalation in powdered form. Such active ingredients include drugs for use in the prophylactic or remedial treatment of the range of conditions known as reversible obstructive airways disease, e.g. asthma and bronchitis. Specific active ingredients which may be mentioned include salts of cromoglycic acid, e.g. sodium cromoglycate; salts of nedocromil, e.g. nedocromil sodium; inhaled steroids such as beclomethasone dipropionate, tipredane, budesonide and fluticasone; anticholinergic agents such as ipratropium bromide; bronchodilators, e.g. salmeterol, salbutamol, reproterol, terbutaline, isoprenaline and fenoterol, and salts thereof. If desired a mixture of active ingredients, for example, a mixture of sodium cromoglycate and a bronchodilator, such as salbutamol, reproterol, isoprenaline, terbutaline, fenoterol or a salt of any one thereof, may be used.

Other active ingredients that may be mentioned include antihistamines, e.g. clemastine, pentamidine and salts thereof, acetyl-β-methylcholine bromide; peptide hormones, e.g. insulin and amylin; bradykinin antagonists; $PLA_2$ inhibitors; PAF antagonists; lipoxygenase inhibitors; leukotriene antagonists; CNS active drugs, e.g. NMDA antagonists, glutamate antagonists, CCK agonists and antagonists; macrolide compounds, e.g. FK 506, rapamycin, cyclosporin and structurally related compounds; vitamins; vaccines, e.g. MMR vaccine and polio vaccine; and vectors for gene therapy, e.g. plasmids containing genes intended to correct genetic disorders such as cystic fibrosis.

The particles of active ingredient incorporated into the medicament compacts preferably have a mass median diameter in the range 0.01 to 15 μm. We prefer that at least 80% w/w and preferably at least 90% w/w of the particles of active ingredient are less than 20 μm, more preferably less than 10 μm, especially less than 7 μm in diameter. The proportion of particles of active ingredient having a diameter in the range 2 to 15 μm is preferably more than 80% w/w.

The particulate active ingredient may be prepared by any suitable technique, as will be known to those skilled in the art. Suitable techniques include milling, e.g. cone milling, or using a hammer or fluid energy mill; micronisation, spray drying and freeze drying.

The medicaments to be compacted according to the invention may comprise a solid pharmaceutically acceptable carrier substance in addition to an active ingredient. The carrier preferably has an effective particle size of from 10 to 100 μm. The term "effective particle size" is used to denote the apparent particle size of a body without distinction as to the number of individual particles which go to make up that body i.e. no distinction is made between a single particle of given size and an agglomerate of the same size which is composed of finer individual particles.

The solid pharmaceutically acceptable carrier in the medicament will generally be a non-toxic material chemically inert to the active ingredient but may, if so desired, also comprise larger particles of the active ingredient. Examples of carriers which may be used in the medicament compacts include dextrans, glucose, mannitol and lactose. A particularly preferred carrier is crystalline lactose.

The particulate carrier may be prepared by grinding the carrier and subsequently separating out the desired fraction by conventional methods, e.g. by air classification and sieving.

The medicament may be prepared by mixing the ingredients together in a mixer, e.g. a planetary or other stirred mixer, prior to formation of the compact according to the process of the invention.

When the medicament comprises a solid carrier, we prefer the proportion of active ingredient to be from 0.1 to 70% w/w, more preferably from 0.1 to 55% w/w, and especially from 5 to 50% w/w of the medicament.

The medicament compacts according to the invention may also contain other ingredients such as flavouring agents, sweetening agents or colourants.

Any conventional pharmaceutically acceptable flavouring agents may be used, particular flavouring agents which may be mentioned include volatile oils, e.g. peppermint oil; and menthol. The proprietary product known by the tradename Dentomint, which contains both peppermint oil and menthol, may also be used. The flavouring agent may be a polysaccharide entrapped flavouring agent such as those disclosed in International Patent Application WO 93/17663. Polysaccharide entrapped flavouring agents are advantageous for use in the compacts produced according to the invention since they are sufficiently resilient to sustain the compression forces required to produce the medicament compacts without releasing the flavouring agent entrapped therein to any significant extent.

Sweetening agents which may be used include any conventional sweetening agents, particular sweetening agents which may be mentioned include saccharin sodium, mannitol, aspartame, cyclamates and sugar.

The medicament compacts produced according to the invention preferably contain a plurality of doses of active ingredient. The actual number of doses incorporated into the compacts will depend inter alia upon the length of the compact, the nature of the active ingredient and the device from which it is to be administered. However, the compacts will typically comprises from 20 to 250, e.g. 112 doses of active ingredient.

The following non-limitative examples illustrate medicament compositions suitable for compaction according to the present invention:

| Ingredients | % w/w |
|---|---|
| Example 1 | |
| Nedocromil sodium (milled) | 50 |
| Flavoured polysaccharide | 5 |
| (85% maltodextrin:15% peppermint oil) | |
| Lactose to | 100 |
| Example 2 | |
| Nedocromil sodium (milled) | 50 |
| Saccharin sodium | 1.25 |
| Lactose to | 100 |
| Example 3 | |
| Nedocromil sodium (milled) | 50 |
| Flavoured polysaccharide | 5 |
| (85% maltodextrin:15% peppermint oil) | |
| Saccharin sodium | 1.25 |
| Lactose to | 100 |

The invention will now be described, by way of example only, with reference to the accompanying drawings, in which:

FIGS. 2A–2E show the stages involved in the production of a medicament compact using the apparatus of FIG. 1.

In the Figures corresponding features of the apparatus for performing the alternative processes are given the same reference numeral.

Figure 1:
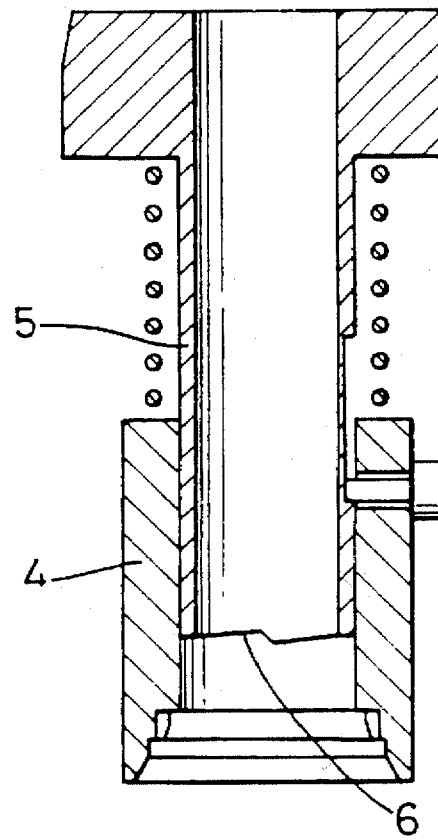
FIG. 1 shows, in longitudinal section, the components of a compaction apparatus for performing the process according to the invention and their mode of assembly.
Figure 1:
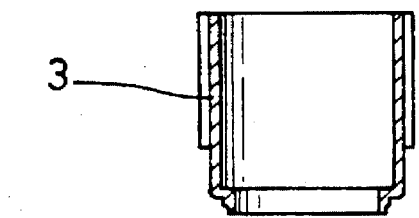
Figure 1:
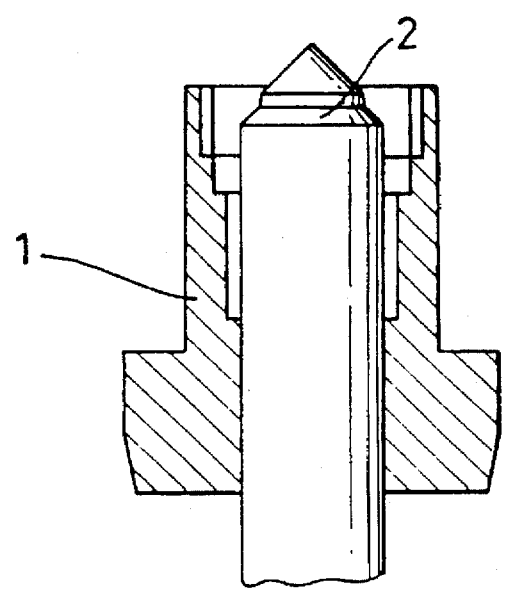

Referring firstly to FIG. 1:

The compaction apparatus comprises a block (1) defining a cylindrical inner space. A cylindrical mandrel (2) having a tapered end is disposed within said inner space and slidably mounted within the block (1). Mould (3) comprising an open ended cylinder is located within block (1), such that mandrel (2) is free to slide along the longitudinal axis of the mould (3). The inner surface of mould (3) and the outer surface of mandrel (2) define the sides of the annular chamber within which the medicament powder is compacted, the bottom of this chamber being defined by a lip on the base of the mould (3).

In use, the block (1) is mounted in a housing (not shown) in which it is free to move vertically. The mandrel (2) is held in the housing thereby preventing its movement relative to the housing.

Cover (4) having a bore identical to the bore of the mould (3) fits over the mould (3) and is be held in position under the action of a spring. A annular compaction sleeve (5), the bore of which is a close fit over the mandrel (2) and the outside diameter of which is a close fit on the inside diameter of the cover (4) mould (3), is located within the bore of cover (4). The packing face (6) of the compaction sleeve (5), which provides the upper limiting wall to the chamber in which the medicament powder is compacted, has a helical profile.

Referring now to FIGS. 2A–2E which illustrate the production of a medicament compact:

Mould (3) is located into the cylindrical inner space of block (1) and a weighed quantity of powdered medicament (7) is placed in the mould (3). The medicament (7) is prevented from falling out of the bottom of mould (3) by the mandrel (2) the tapered end of which projects through the base of the mould (3) s FIG. 2A.

Cover (4) and compaction sleeve (5) are then placed on the block (1) and held in place by spring force—FIG. 2B.

The medicament (7) is distributed around the mandrel (2) by the application of vertical vibration to the mandrel (2). The vibration is continued as block (1), mould (3), cover (4) and compaction sleeve (5) are lowered around the mandrel (2) thus levelling the surface of the powder before compaction. The vibration is then turned off—FIG. 2C.

The block (1), mould (3) and cover (4) are then lifted together whilst the mandrel (2) and compaction sleeve (5) remain stationary. The packing face (6) of is the compaction sleeve (5) is thus urged against the powdered medicament (7) contained in the mould (3) and the powdered medicament (7) is thus compacted. During the compaction process the frictional force between the medicament (7) and the mould (3) in a direction parallel to the longitudinal axis of the mould (3) is directed upwards towards the compaction sleeve (5), and the frictional force between the medicament (7) and the mandrel (2) in a direction parallel to the longitudinal axis of the mould (3) is directed downwards towards the base of the mould (3). The degree of movement and hence the compacted height of the medicament (7) is determined by the drive means (not shown) which is programmed for the particular compaction height—FIG. 2D.

The cover (4) and compaction sleeve (5) are then lifted off the block (1). The mould (3) containing the compacted body of powdered medicament (8) can then be removed from the block (1) and assembled directly into a medicament inhalation device, the mould (3) being adapted to form all or part of the medicament reservoir of the medicament inhalation device—FIG. 2E.

Figure 3A:
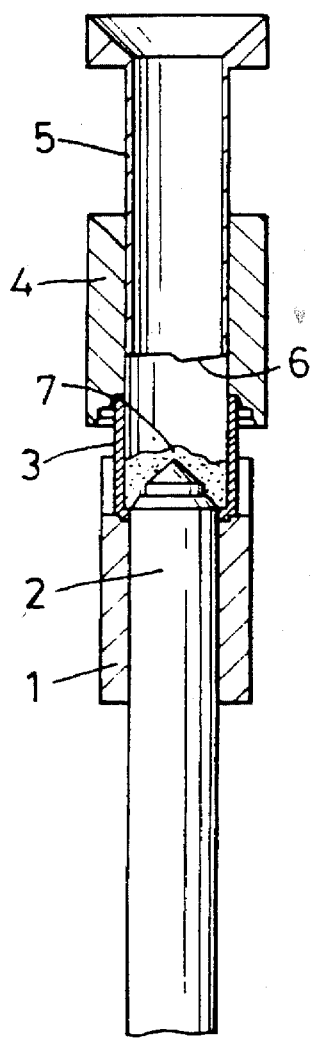
FIGS. 3A–3C show schematically the stages involved in the production of a medicament compact according to the invention in which the relative movement of the mandrel and the mould is increased.
Figure 3B:
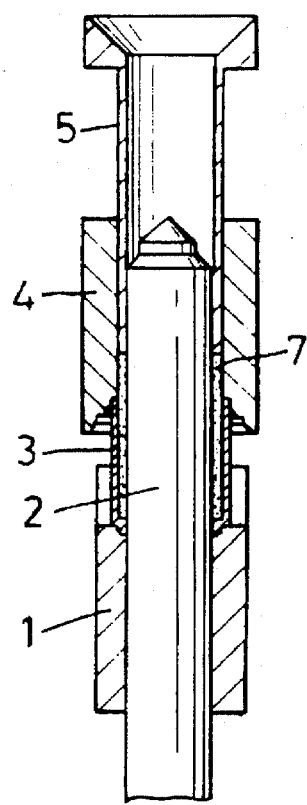
Figure 3C:
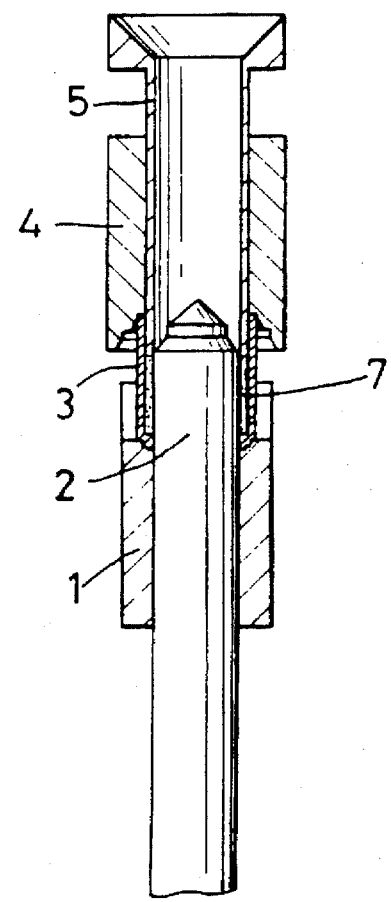

Referring now to FIGS. 3A–3C, which illustrate a compaction process in which the distance moved by the mould (3) relative to mandrel (2) is greater than in the process shown in FIG. 2:

As in FIG. 2, a weighed quantity of powdered medicament (7) is placed in the mould (3) around the tapered end of mandrel (2). Cover (4) and compaction sleeve (5) are then fitted in place—FIG. 3A.

The block (1), mould (3), cover (4) and compaction sleeve (5) are lowered around the mandrel (2) which is held stationary. In this process the mould (3) is lowered further around the mandrel (2) than in FIG. 2, so that the mandrel (2) projects inside the compaction sleeve (5)—FIG. 3B.

Mould (3) and cover (4) are moved up the mandrel (2) together, at the same time the compaction sleeve (5) is also moved upwards but through a smaller distance than the mould (3). Hence the mould (3) converges on the compaction sleeve (5) and the powder (7) is compacted—FIG. 3C.

We claim:

1. A process for the production of a medicament compact, comprising the steps of:

a) placing loose powdered medicament in a mould (3) having a longitudinal axis, b) positioning a mandrel (2) along the longitudinal axis of the mould (3); and c) compressing the medicament by applying a force parallel to the longitudinal axis such that during compression the frictional force between the medicament and the mould (3) and the frictional force between the medicament and the mandrel (2) are in opposite directions parallel to the longitudinal axis.

2. A process according to claim 1, wherein the mould (3) and the mandrel (2) move relative to one another in a direction parallel to the longitudinal axis during the compression process.

3. A process, according to claim 2, wherein relative movement of the mould (3) and mandrel (2) is achieved by fixing the position of the mandrel (2) and moving the mould (3) in a direction parallel to the longitudinal axis during the compression process.

4. A process according to claim 1 in which the surface of the powder is levelled prior to compaction.

5. A process according to claim 1, wherein the end of the mandrel (2) is tapered.

6. A process according to claim 1, wherein the mandrel (2) is vibrated as it positioned along the longitudinal axis of the mould (3).

7. A process according to claim 1, wherein the powder is compacted by compaction means (5) having a compacting face provided with a helical profile (6).

8. A process according to claim 1, wherein the medicament compact (8) is formed in a mould (3) which subsequently forms all or part of a medicament reservoir of a medicament inhalation device.

* * * * *

UNITED STATES PATENT AND TRADEMARK OFFICE
CERTIFICATE OF CORRECTION

PATENT NO. : 5,670,167
DATED : September 23, 1997
INVENTOR(S) : Clive Roland Sleath, et. al.

It is certified that error appears in the above-identified patent and that said Letters Patent is hereby corrected as shown below:

In the Claims:

In claim 6, line 53, please insert --is-- after the word "it".

Signed and Sealed this

Sixteenth Day of June, 1998

*Attest:*

BRUCE LEHMAN

*Attesting Officer*     *Commissioner of Patents and Trademarks*